United States Patent [19]

Tomich et al.

[11] Patent Number: 5,922,840
[45] Date of Patent: Jul. 13, 1999

[54] METHODS FOR PURIFYING SYNTHETIC PEPTIDES

[75] Inventors: John M. Tomich; Takeo Iwamoto, both of Manhattan, Kans.

[73] Assignee: Kansas State University Research Foundation, Manhattan, Kans.

[21] Appl. No.: 08/685,279

[22] Filed: Jul. 23, 1996

[51] Int. Cl.$^6$ ................................................. A61K 38/04
[52] U.S. Cl. ......................... 530/344; 530/345; 525/54.1
[58] Field of Search ................................... 530/334, 535; 525/54.1

[56] References Cited

U.S. PATENT DOCUMENTS 5,648,462  7/1997  Funakoshi ............................... 530/344

OTHER PUBLICATIONS

Lu et al., "Pegylated Peptides I" Caplus # 1995: 21746, 1994.
Zier et al., "Polyethylene Glycol in Solid Phase Synthesis" Caplus # 1994: 656271.
Lu et al., "Pegylated Peptides II" Caplus # 1993: 671693.
Brown et al.; (17–Tetrabenzo [a,c,g,i] fluorenyl) methylchloroformate (TbfmocCl) a Reagent for the Rapid and Efficien Purification of Synthetic Peptides and Proteins; Tetrahedron vol. 51, No. 43, pp. 11815–11830(1995).
Quesnel e al.; Purification of Synthetic Peptide Libraries by Affinity Chromatography Using the Avidin–Biotin System; Analytical Biochemistry 231, pp. 182–187 (1995).
Bayer et al.; New polymer supports for solid–liquid–phase peptide synthesis; Chemistry of Peptides and Proteins, vol. 3 (1985).
Kazmierski et al.; Synthesis of the carbonic acid benzotrinzol–1–yl–ester–(2–biotinylamino)–9H–fluoren–9–ylmethyl ester: a convenient transient–diotinylation reagent for use in affinity chromatography; Tetra. Letters, vol. 36, No. 50, pp. 9097–9100 (1995).
Nokihara et al.; Rapid and efficient preparation of affinity columns, in which peptides as ligands are bound to the solid–phase support; Peptide Chemistry 1993: Y. Okada (Ed.) (1994); pp. 25–28.
Funakoshi et al.; Affinity purification method using a reversible biotinylating reagent for peptides synthesized by the solid–phase technique; J. Chromatog, 638 (1993) 21–27.
Bianchi et al.; Affinity purification of a difficult–sequence protein; In the. J. Peptide Protein Res. 42, 1993, 93–96.
Bayer et al.; Liquid Phase Synthesis of Peptides; Nature, vol. 237, Jun. 30, 1972.

*Primary Examiner*—Avis M. Davenport
*Assistant Examiner*—Patrick R. Delaney
*Attorney, Agent, or Firm*—Hovey, Williams, Timmons & Collins

[57] ABSTRACT

Methods for making preparations of homogenous peptides are disclosed. In these methods, reversible alterations of the physicochemical properties of the peptides are exploited. In preferred embodiments, the methods include the following sequential steps: (1) exhaustive capping is carried out during solid-phase synthesis of a desired peptide; (2) a cleavable linker is attached to the peptide, (3) a polymer is added to the peptide either by condensation with preformed polymer or by in situ polymerization such that the linker is interposed between the polymer moiety and the peptide moiety of the resultant adduct; alternatively, steps (2) and (3) can be conducted simultaneously by attaching a combination polymer/linker to the peptide; (4) the polymer-peptide adduct is cleaved from the resin; (5) the polymer-peptide adduct is purified from undesired, nonadducted peptides; and (6) the polymer-peptide adduct is cleaved at the linker, and the desired peptide is purified from the polymer. In some cases, it may be desirable to omit step (6) in order to leave the polymer moiety attached to the desired peptide. For example, the polymer-peptide adducts of the present invention are very soluble in water, and therefore can be used to solubilize amphipathic peptides. Additionally, the polymer moieties of the polymer-peptide adducts can elicit immune responses in mammals or birds; thus, the adducts and corresponding antibodies can be used in research protocols to track the peptide moieties of the adducts.

26 Claims, 14 Drawing Sheets

METHODS FOR PURIFYING SYNTHETIC PEPTIDES

BACKGROUND OF THE INVENTION

1. Field of the Invention

The present invention is broadly concerned with methods for purifying synthetic peptides in which reversible alterations of the physicochemical properties of the peptides are exploited. More particularly, in preferred embodiments, a polymer is added to a desired peptide either by condensation with preformed polymer or by in situ polymerization such that a cleavable linker is interposed between the polymer moiety and the peptide moiety of the resultant polymer-peptide adduct; the adduct is then easily purified from undesired, nonadducted peptides since the adduct and the nonadducted peptides have different solubility characteristics; subsequently, the adduct may be cleaved at the linker and the desired peptide purified from the polymer.

2. Description of the Prior Art

The demand for synthetic peptides in many research fields has increased in recent years, particularly since the advent of solid-phase peptide synthesis. For example, in immunochemistry, peptides as epitopes of proteins are important for antibody production. Also, peptides are often used as ligands in affinity chromatography.

In solid-phase peptide synthesis, amino acids are coupled in stepwise fashion to a peptide attached to an insoluble support contained within a reaction vessel. The insoluble support is composed of a resin which is typically polystyrene. Each successive coupling of an amino acid is carried out by passing the amino acid through the reaction vessel. The amino acid is "protected," i.e., it has a stable but reversible blocking group attached to it which prevents polymerization of that amino acid. Suitable reversible blocking groups include benzyloxycarbonyl, t-butyloxycarbonyl (BOC), and 9-fluorenylmethoxycarbonyl (Fmoc) groups. After the amino acid is coupled to the peptide, the reversible blocking group is removed to allow addition of another amino acid to the peptide.

Amino acid coupling reactions are highly efficient; more than 99% of the peptides have an amino acid added to them during each coupling cycle. However, a small percentage of the peptides fail to receive an amino acid during each coupling cycle; these peptides, referred to as "failed sequences," represent a serious problem in the synthesis of peptides. A 1% failure rate per coupling cycle gives a significant amount of failed sequences at the end of a synthesis having multiple cycles.

For example, a failure rate of 1% per cycle in the syntheses of a 30-residue peptide (29 cycles) and a 50-residue peptide (49 cycles) generates greater than 22% and 39% by weight of failed sequences, respectively, in the final mixtures. Furthermore, a variety of failed sequences different from each other are generated which may be deficient in as little as one residue as compared with the target peptide. It is very difficult, if not impossible, to separate the target peptide from the failed sequences using normal separation techniques since the target peptide and the failed sequences may have nearly identical physicochemical properties. Typically, specifications for peptides call for a purity ranging from 95 to 98%. This level of purity can be attained for peptides having less than 30 residues using high performance liquid chromatography (HPLC) as the purification method. However, this level of purity cannot be attained for larger peptides using HPLC or other state-of-the-art purification techniques.

In the past, this separation problem has been alleviated somewhat by passing a "capping" reagent through the reaction vessel in order to "cap" failed sequences. The presence of the reversible blocking group on a coupled amino acid prevents capping of the elongating target peptide. This cap prevents failed sequences from participating in subsequent coupling cycles. Thus, the sequences that fail early in the peptide synthesis are substantially shorter than the target peptide and therefore have different physicochemical properties that can be exploited in separation techniques. Typical capping reagents include acetic anhydride and 4-methoxybenzoic acid.

Despite the use of capping reagents, separation of the target peptide from failed sequences remains a serious problem. Affinity chromatography methods have been proposed wherein a target peptide is biotinylated while failed sequences are not [*Journal of Chromatography*, 638:21–27 (1993); *Tetrahedron Letters*, 36:9097–9100 (1995)]. The biotinylated peptide and the failed sequences are then cleaved from the support and passed through an expensive avidin-agarose column to adsorb the biotinylated peptide. The adsorbed biotinylated peptide is then eluted from the column and treated with base to release the biotin moiety and yield the target peptide. These methods have not gained wide acceptance because the presence of the biotin moiety does little to alter the physicochemical properties of the target peptide, and the avidin-agarose column is very expensive and has a limited life-time.

There is accordingly an unsatisfied need in the art for a method for the synthesis and purification of peptides which is simple, uses relatively inexpensive reagents, and provides the desired peptide in good yield and at a high level of purity.

SUMMARY OF THE INVENTION

The present invention overcomes the problems outlined above by providing methods for making preparations of homogenous peptides (i.e., preparations which are not contaminated with peptides having undesired sequences). In these methods, reversible alterations of the physicochemical properties of the peptides are exploited. Resultant peptides may include greater than 30 amino acid residues, and may be helical amphipathic peptides.

In preferred embodiments, these methods comprise the following steps: (a) providing a reaction zone including an immobilizing support, (b) passing a respective amino acid unit through the reaction zone, (c) repeating step (b) with each of a plurality of amino acid units, thereby constructing a chain of peptide-bonded amino acid residues, wherein the chain presents a C-terminal end bound to the support and an opposed free end, (d) producing a polymer-peptide adduct including a polymer moiety attached to the free end of the chain, wherein the polymer moiety has a plurality of repeating chemical groups, and (e) cleaving the adduct from the support.

The respective amino acid unit in step (b) preferably includes an amino acid residue having an attached reversible blocking group (e.g., a Fmoc group) which prevents multiple attachments of the respective amino acid unit to the free end of the chain. This reversible blocking group is detached from the respective amino acid unit after step (b), thereby allowing attachment of another amino acid unit to the elongating chain. Advantageously, a capping reagent (e.g., 4-methoxybenzoic acid or acetic anhydride) is passed through the reaction zone before the reversible blocking group is detached so that, if the respective amino acid unit did not attach to the free end of the chain (resulting in a truncated sequence), the chain is capped and rendered inert throughout the rest of the peptide synthesis.

Ideally, the polymer moiety (e.g., a polyalkylene glycol, a polyamide, a polystyrene, a polyester, a polyacrylamide, a polyalcohol, an oligopeptide, an oligosaccharide, an oligonucleotide, or a mixture thereof) is formed in step (d) by attaching a preformed polymer to the free end of the chain. Alternatively, the polymer moiety is formed by the in situ polymerization of a monomer at the free end of the chain.

Advantageously, the polymer-peptide adduct is separated from nonadducted peptides having undesired sequences. After addition of the polymer moiety, the adduct and the undesired nonadducted peptides have significantly different solubility characteristics in a selected solvent. Thus, this solvent can be used in an aqueous extraction procedure to purify the adduct from the undesired peptides.

The polymer moiety is preferably removed from the adduct to yield the desired peptide. To facilitate removal of the polymer moiety, a cleavable linker (e.g., a methionine residue) is attached to the free end of the chain prior to step (d), whereby, after step (d), the linker is interposed between the free end of the chain and the polymer moiety. A combination polymer/linker molecule (e.g., poly-2-amidofluorenyl-9-methoxycarbonyl chloride) may be used to simultaneously attach a preformed polymer and a linker to the free N-terminal end of the chain.

DETAILED DESCRIPTION OF THE PREFERRED EMBODIMENTS

The present invention provides a relatively simple method for making preparations of homogenous peptides in which reversible alterations of the physicochemical properties of the peptides are exploited. The general scheme for making a desired peptide by this method includes the following sequential steps: (1) exhaustive capping is carried out during solid-phase synthesis of the peptide; (2) a cleavable linker is attached to the peptide, (3) a polymer is added to the peptide either by condensation with preformed polymer or by in situ polymerization such that the linker is interposed between the polymer moiety and the peptide moiety of the resultant adduct; alternatively, steps (2) and (3) can be conducted simultaneously by attaching a combination polymer/linker to the peptide; (4) the polymer-peptide adduct is cleaved from the resin; (5) the polymer-peptide adduct is purified from undesired, non-adducted peptides; and (6) the polymer-peptide adduct is cleaved at the linker, and the desired peptide is purified from the polymer.

However, there may be instances in which it is desirable to leave the polymer moiety attached to the desired peptide, in which case step (6) will be omitted from the protocol. Furthermore, step (2) can be omitted if there is no need to remove the polymer moiety from the desired peptide; in this case, the polymer can be attached directly to the desired peptide. For instance, transmembrane peptides that function as ion channels contain amphipathic helices having opposed hydrophilic and hydrophobic faces. In aqueous environments, these peptides have a strong tendency to clump together to form insoluble aggregates. Thus, these peptides are difficult to insert into cell membranes. However, polymer-peptide adducts are very soluble in water, and therefore can be used to insert the peptide moieties thereof into cell membranes. Additionally, the polymer moieties can elicit immune responses in mammals or birds. Thus, the adducts and corresponding antibodies can be used in research protocols to track the peptide moieties of the adducts.

Figure 1:
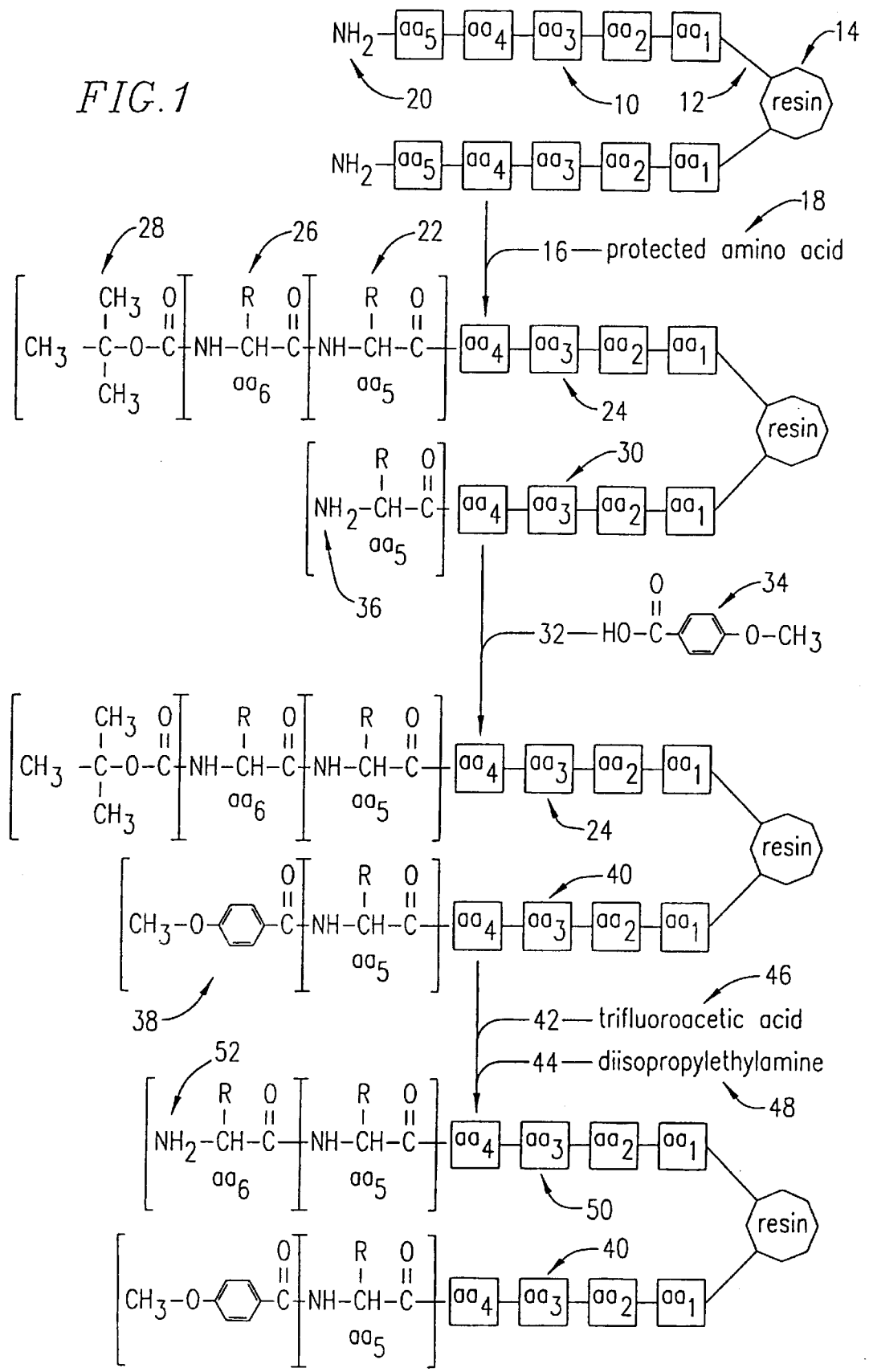
FIG. 1 is a flow chart illustrating one cycle of a stepwise, solid-phase method of peptide synthesis in accordance with the present invention.

FIG. 1 illustrates one coupling cycle of the stepwise, solid-phase method of peptide synthesis used in the present invention to make a target peptide. A partial sequence 10 initially having five amino acid residues ($aa_1$ through $aa_5$) is bound at its C-terminus 12 to a resin support 14. The partial sequence 10 was synthesized in cycles previous to the illustrated cycle. The resin 14 is contained within a vessel to form a reaction zone. Polystyrene beads are a preferred resin, although a variety of other resins can be employed.

In the first step 16 of the illustrated coupling cycle, a protected amino acid 18 is passed through the reaction zone in order to couple it to the N-terminus 20 of $aa_5$ 22. A vast majority (greater than 99%) of partial sequences 10 receive a protected amino acid 18 to form new sequences 24. The protected amino acid 18 includes an amino acid moiety $aa_6$ 26, and a reversible blocking group 28 which prevents multiple attachments of $aa_6$ 26 to the partial sequence 10. A preferred reversible blocking group is the Fmoc group, although a number of other reversible blocking agents can be used. A small minority (from about 0.5 to 1%) of the partial sequences 10 fail to receive a protected amino acid 18 and thereby become failed sequences 30.

In the next step 32, a capping reagent 34, in this case 4-methoxybenzoic acid, is passed through the reaction vessel in order to cap the failed sequence 30. 4-methoxybenzoic acid is the preferred capping reagent because it reacts efficiently with the N-terminus 36 of the failed sequence 30, and thereby adds a cap 38 to the failed sequence 30 to give a capped failed sequence 40. However, 4-methoxybenzoic acid does not react with the Fmoc-protected sequence 24. In current practice, a 10X molar excess of 4-methoxybenzoic acid (relative to the molarity of the peptide) is added to the reaction zone, and the capping reaction is allowed to proceed for 2 hours at room temperature.

In steps 42 and 44, trifluoroacetic acid 46 and diisopropylethylamine 48, respectively, are sequentially passed through the reaction vessel in order to remove the reversible blocking group 28 from the sequence 24, resulting in the formation of a sequence 50 having a free N-terminus 52. Steps 42 and 44 have no effect on the capped failed sequence 40 which remains inert throughout the rest of the peptide synthesis. The N-terminus 52 of sequence 50 is fully reactive in that it can receive an additional protected amino acid 18. Additional amino acid residues are added to the sequence 50 by repeating steps 16, 32, 42, and 44 using respective protected amino acids 18.

Once the synthesis of the target peptide is complete and before a polymer is added to the target peptide to form a polymer-peptide adduct, a cleavable linker (preferably a methionine linker) is attached to the N-terminus of the target peptide. After addition of the linker, the polymer is attached to the linker. Thus, the resultant polymer-peptide adduct has a linker interposed between the polymer moiety and peptide moiety of the adduct. Subsequent cleavage at linker liberates the target peptide from the adduct.

Figure 2:
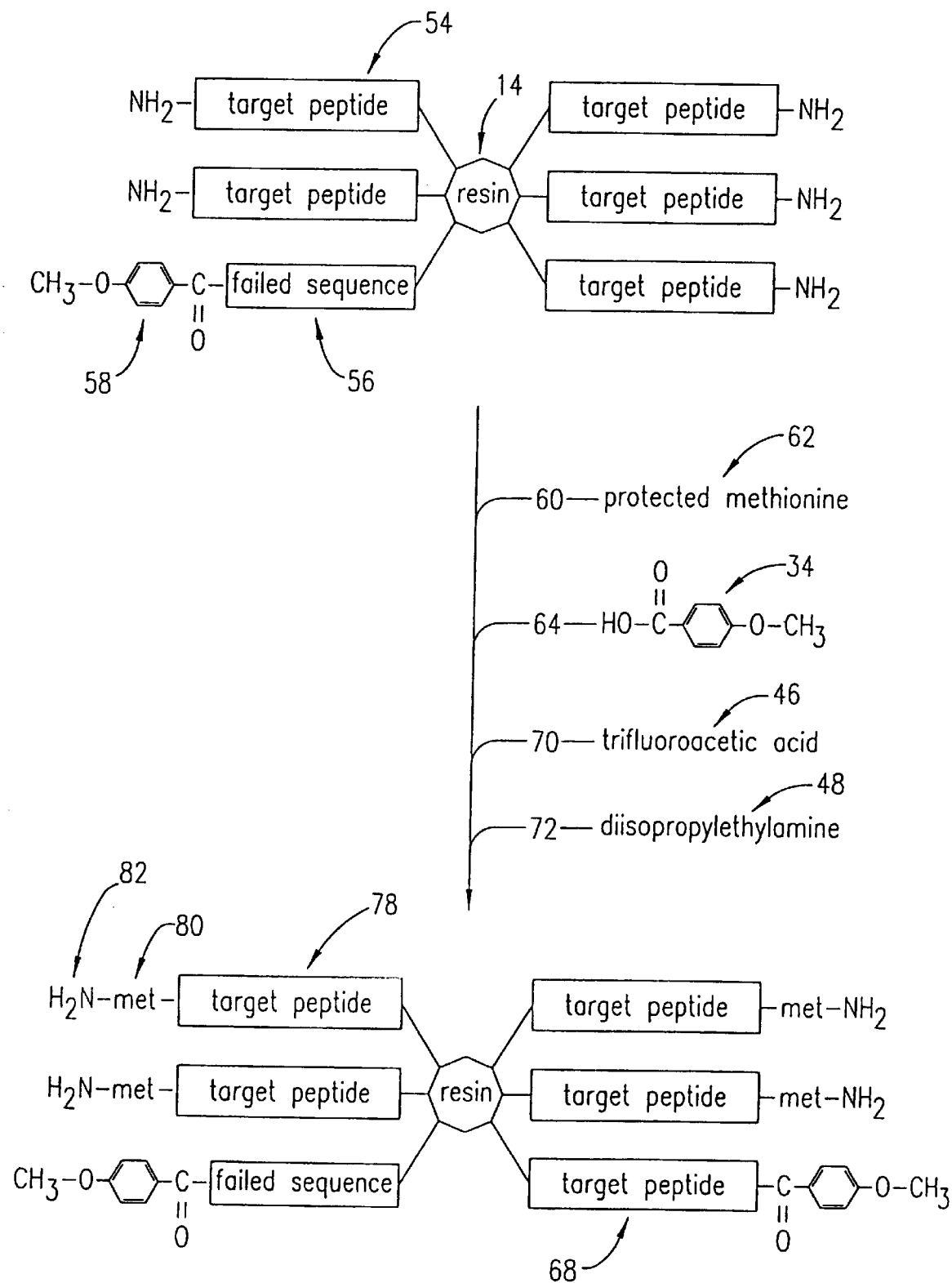
FIG. 2 is a flow chart illustrating a method of attaching a methionine linker to a target peptide in accordance with the present invention.

FIG. 2 illustrates the addition of a methionine linker to a target peptide 54 which was synthesized as shown in FIG. 1. The methionine linker is added to the target peptide 54 while it is still attached to the resin 14. FIG. 2 also shows a capped failed sequence 56 which does not receive a methionine linker due to the presence of the cap 58. In step 60, a protected methionine 62 is passed through the reaction zone in order to couple it to the N-terminus of the target peptide 54. As with the protected amino acid 18 (FIG. 1), the protected methionine 62 includes an amino acid moiety and a reversible blocking group (not shown).

In step 64, a capping reagent 34, again 4-methoxybenzoic acid, is subsequently passed through the reaction vessel in order to cap any target peptide 54 which did not receive a protected methionine 62. This capping reaction results in a capped target peptide 68. In steps 70 and 72, trifluoroacetic acid 46 and diisopropylethylamine 48, respectively, are sequentially passed through the reaction vessel in order to remove the reversible blocking group from the target peptide 54 which received a protected methionine 62, resulting in a target peptide 78. Thus, the resultant target peptide 78 has a methionine residue 80 (i.e., a methionine linker) at its N-terminus 82. Furthermore, this N-terminus 82 is free of a reversible blocking group or a cap.

After addition of a linker, a polymer is added to the target peptide to form a polymer-peptide adduct. Suitable polymers include polyalkylene glycols (e.g., PEG 600), polyamides, polystyrenes, polyesters, polyacrylamides, polyalcohols, oligopeptides, oligosaccharides, oligonucleotides and mixtures thereof. This polymer-peptide adduct is formed either by in situ polymerization of a monomer at the N-terminus of the peptide, or more preferably, by condensation of a preformed polymer with the N-terminus of the peptide. The polymer moiety of the adduct gives the adduct physicochemical properties different than the physicochemical properties of the failed sequences arising during peptide synthesis. These properties are exploited in the purification of the adduct from the failed sequences. Furthermore, if a cleavable linker (e.g., a methionine linker) was interposed between the polymer moiety and the peptide moiety, the adduct can be cleaved at the linker after purification from the failed sequences to yield the target peptide.

Figure 3:
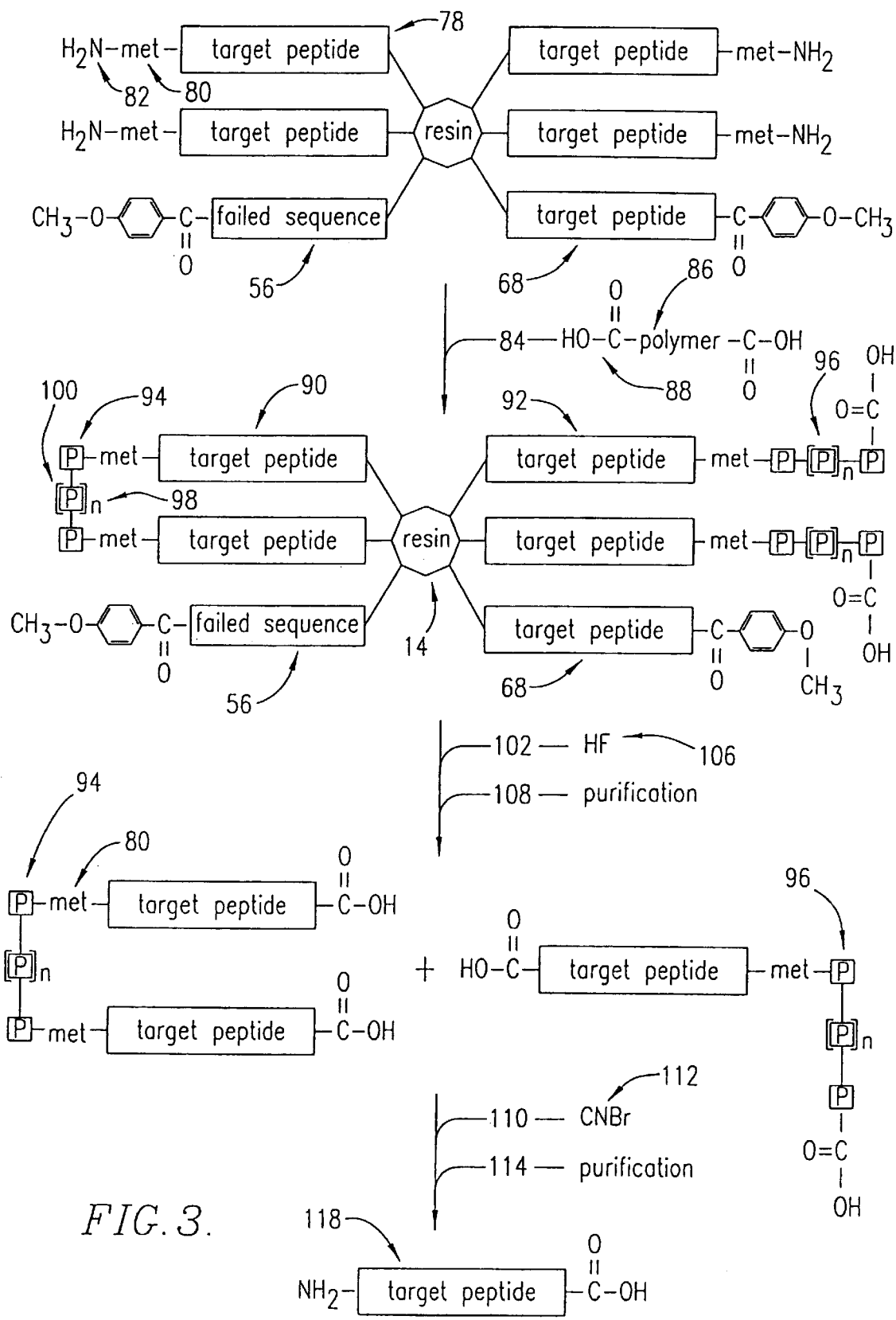
FIG. 3 is a flow chart illustrating a condensation method of adding a polymer to a target peptide having an attached methionine linker in accordance with the present invention.

FIG. 3 illustrates the condensation of a preformed polymer with the target peptide 78, which was synthesized as shown in FIGS. 1 and 2. This target peptide 78 has a methionine linker 80 at its N-terminus 82. In step 84, a preformed polymer 86 is passed through the reaction vessel, wherein the carboxyl group 88 of the preformed polymer 86 reacts with the N-terminus 82 of the target peptide 78. Two types of polymer-peptide adducts are thereby formed. In one type, the adduct 90 is composed of two peptide moieties 91 which are crosslinked at their N-termini with a polymer moiety 94. In the other type, the adduct 92 is composed of a single peptide moiety 91 having a polymer moiety 96 at its N-terminus. As shown in FIG. 3, a number 98 of polymer units 100 may be linked to a pair of peptide moieties 91 or to an individual peptide moiety 91 to form adducts 90 and 92, respectively.

In step 102, all peptides and polymer-peptide adducts attached to the resin 14 are cleaved at their C-termini 12 with hydrogen fluoride 106, and are thereby detached from the resin 14. The adducts 90 and 92 are purified in step 108 from the capped failed sequences 56 and the capped target peptides 68 which have not received the polymer 86. The purification step 108 exploits the physicochemical properties imparted to the adducts 90 and 92 by the polymer moieties 94 and 96, respectively. For example, the polymer moieties 94 and 96 may make the adducts 90 and 92, respectively, soluble in a particular solvent while peptides which are not adducted to the polymer 86 are insoluble in that solvent. Thus, the adducts 90 and 92 may be separated from the nonadducted peptides by aqueous liquid extraction procedures utilizing that solvent. Alternatively, the polymer moieties 94 and 96 may alter the chromatographic behavior of the adducts 90 and 92, respectively, such that the retention time for the adducts 90 and 92 in reverse-phase high-performance liquid chromatography is distinct from that of nonadducted peptides.

After the adducts 90 and 92 are purified in step 108, they are cleaved at their methionine linkers 80 in step 110 using CNBr 112. In step 114, the resultant target peptide 118 is purified using, for example, an appropriate gel filtration column. After this purification step, the target peptide 118 is ready for use.

Figure 4:
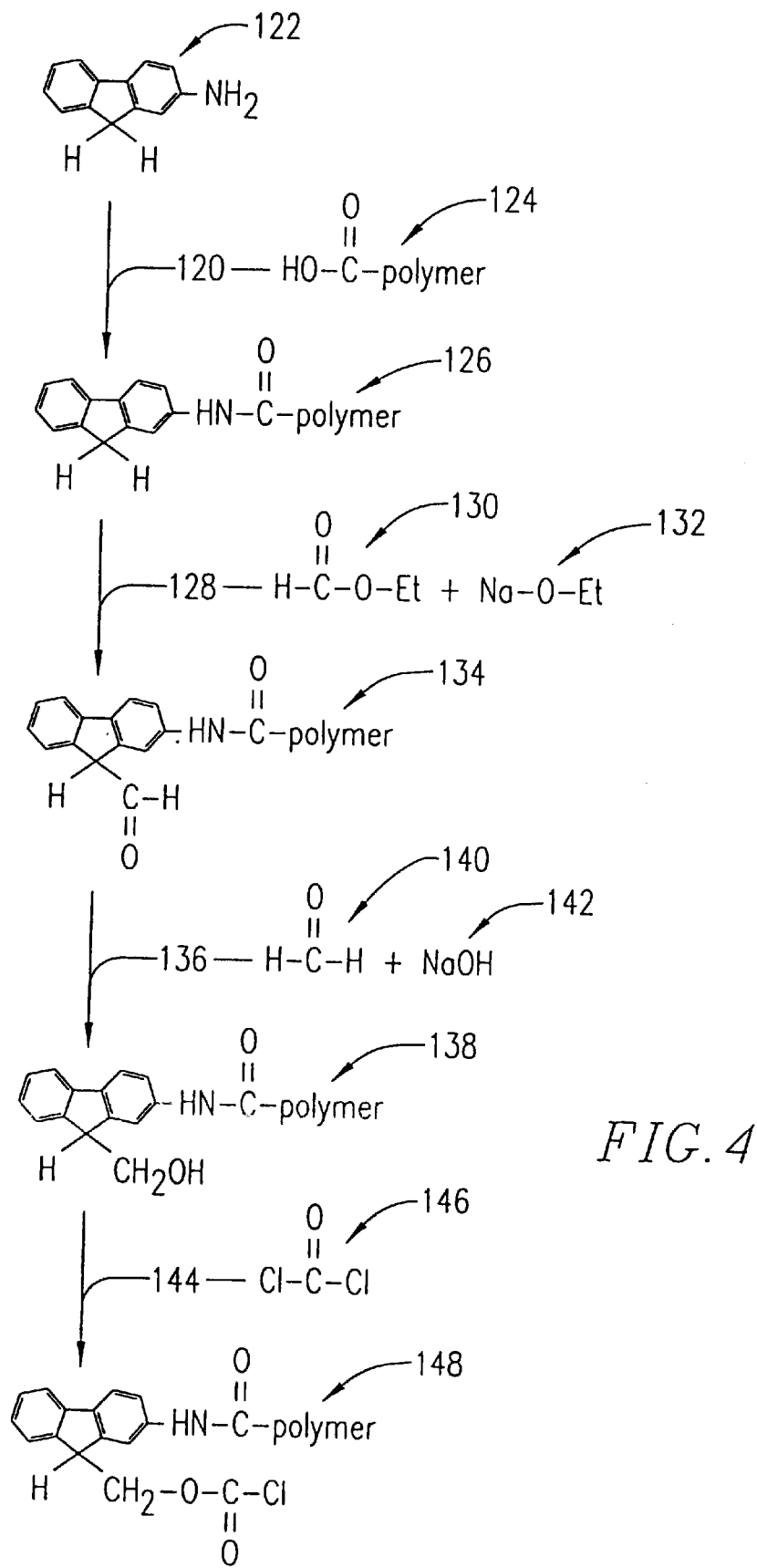
FIG. 4 is a flow chart illustrating a method of synthesis of a linker/polymer molecule in accordance with the present invention.

An alternative polymer condensation approach makes use of a molecule that serves as both a polymer and a cleavable linker. When this approach is employed, the polymer and the linker are added to the target peptide in a single step. FIG. 4 illustrates the synthesis of one such polymer/linker. In step 120 of this synthesis, 2-amino fluorene 122 is coupled with a polymer 124 to form a poly-2-amidofluorene-polymer adduct 126. In this reaction, a 10- to 50-fold molar excess of the polymer 122 is used (relative to the molarity of 2-amino fluorene 122). An amide bond is formed as the 1-Hydroxybenzotriazole (HOBt) ester using dicyclohexylcarbodiimide as the condensing agent in the solvent dimethylformamide. In step 128, the poly-2-amidofluorene-polymer adduct 126 is reacted with ethyl formate 130 and sodium ethoxide 132 to yield poly-2-amido-9-formylfluorene 134. Using the Cannizzaro reaction in step 136, poly-2-amido-9-formylfluorene 134 is converted to poly-2-amidofluorenyl-9-methanol 138 in the presence of formaldehyde 140 and sodium hydroxide 142. In step 144, phosgene 146 is condensed with poly-2-amidofluorenyl-9-methanol 138 to form the polymer/linker poly-2-amidofluorenyl-9-methoxycarbonyl chloride 148.

Figure 5:
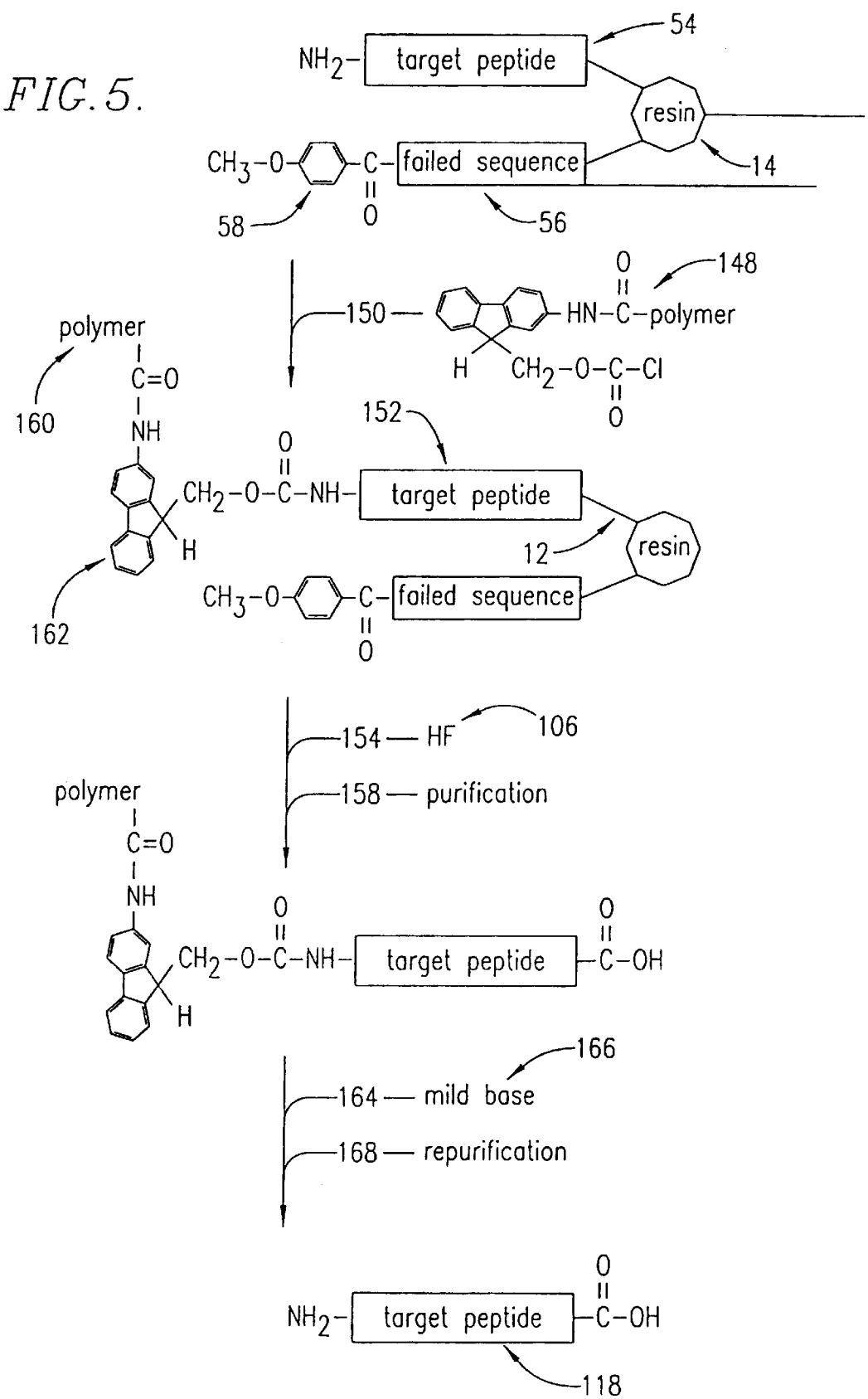
FIG. 5 is a flow chart illustrating a condensation method of adding a linker/polymer molecule to a target peptide in accordance with the present invention.

FIG. 5 illustrates the steps involved in the addition of this polymer/linker 148 to the target peptide 54 which was synthesized as shown in FIG. 1. In step 150, the polymer/linker 148 is added to the target peptide 54 while it is still attached to the resin 14. The resultant product is a polymer/linker-peptide adduct 152. FIG. 5 also shows a capped failed sequence 56 which does not receive the polymer/linker 148 due to the presence of the cap 58. In step 154, all peptides and polymer/linker-peptide adducts attached to the resin 14 are cleaved at their C-termini 12 with hydrogen fluoride 106, and are thereby detached from the resin 14. The adduct 152 is purified in step 158 from the capped failed sequences 56 which did not receive the polymer/linker 148. In step 158, the physicochemical properties imparted to the adduct 152 by the polymer moiety 160 are exploited as described above. After the adduct 152 is purified in step 158, it is cleaved at its polymer/linker moiety 162 in step 164 using mild base 166. In step 168, the resultant target peptide 118 is purified.

Polymer/linkers such as poly-2-amidofluorenyl-9-methoxycarbonyl chloride have many advantages over traditional linkers. They can be used with any peptide regardless of the amino acid composition. Conversely, methionine linkers are useful only if the target peptide is devoid of methionine residues, since CNBr cleaves peptides at all methionine residues. Also, these polymer/linkers are removed from the polymer/linker-peptide adduct by the addition of a mild base which has no negative effects on the released target peptide.

Figure 6:
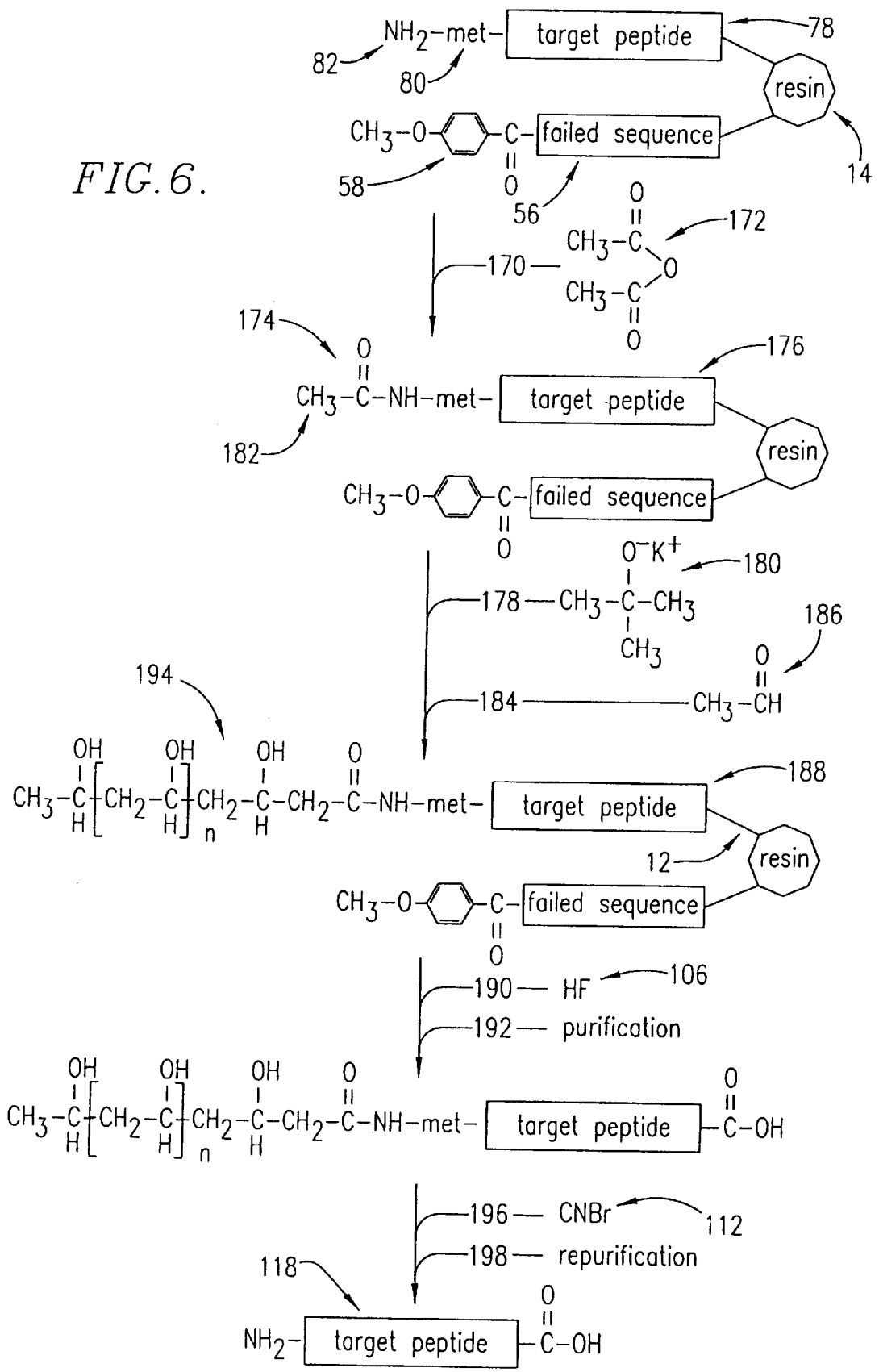
FIG. 6 is a flow chart illustrating an in situ polymerization method of adding a polymer to a target peptide having an attached methionine linker in accordance with the present invention.

The in situ polymerization method for adding a polymer to a target protein is illustrated in FIG. 6. The target peptide 78, which was synthesized as shown in FIGS. 1 and 2, has a methionine linker 80 at its N-terminus 82. In step 170, acetic anhydride 172 is passed through the reaction vessel in order to cap the target peptide 78 with an acetyl group 174. In this reaction, an acetylated target peptide 176 is formed. The acetyl group 174 serves as the initiation site for the in situ polymerization reaction. FIG. 6 also shows a capped failed sequence 56 which does not receive an acetyl group 174 due to the presence of the cap 58. In step 178, a slight molar excess (105%) of the initiator potassium t-butoxide 180 (relative to the molarity of the acetylated target peptide 176) is added to the reaction vessel and allowed to react with the acetylated target peptide 176 at a temperature of 0° C. for 2 minutes in order to activate the terminal methyl group 182. In step 184, an acetaldehyde monomer 186 is gradually added to the reaction vessel over a period of 15 minutes until about a 100X molar excess is present (relative to the molarity of the acetylated target peptide 176).

The polymerization reaction is then allowed to proceed first at 0° C. for 2 hours, and then at room temperature for 2 to 24 hours, resulting in the formation of a polymer-peptide adduct 188. The polymerization reaction is stopped by adding ethyl acetate or ether, and the resin is then filtered. The resin is subsequently washed with dichloromethane, and the dichloromethane fraction is pooled with the ethyl acetate or ether fraction. The pooled fraction is saved for later analysis. The resin is then dried and washed with water to remove any water-soluble materials, and the aqueous fraction is also saved. The resin is again dried and weighed to determine weight gain due to the polymerization reaction. The organic, water, and small resin fraction are analyzed for peptide content as follows: Known sample volumes are dried in vacuo and are then subjected to gas-phase hydrolysis using constant boiling hydrochloric acid at 165° C. for 2 hours; the samples are then analyzed for the presence of free amino acids.

In step 190, all peptides and polymer-peptide adducts attached to the resin 14 are cleaved at their C-termini 12 with hydrogen fluoride 106, and are thereby detached from the resin 14. The adduct 188 is purified in step 192 from the capped failed sequences 56, wherein the physicochemical properties imparted to the adduct 188 by the polymer moiety 194 are exploited. After the adduct 188 is purified in step 192, it is cleaved at its methionine linker 80 in step 196 using CNBr 112. In step 198, the resultant target peptide 118 is purified.

Actual practice with the in situ polymerization strategy demonstrated that the polymer moiety of the polymer-peptide adduct was attached only to the N-terminus of the peptide moiety. After about 24 hours of reaction time, the length of the polymer moiety was found to be about 15 alcohol residues, while the molecular weight of the polymer moiety was about 750 Da. When the peptide moiety was itself water insoluble, addition of a polyalcohol tail 15 residues in length rendered the adduct soluble, suggesting that 15 alcohol residues is more than adequate to alter the physicochemical properties of the target peptide.

EXAMPLE

The following example describes the synthesis and purification of a model polymer-peptide adduct, namely, an adduct including a preformed polymer moiety composed of PEG 600, a methionine linker, and a peptide moiety 12 amino-acid residues in length. This example is set forth by way of illustration only, and nothing therein shall be taken as a limitation of the overall scope of the invention.

Materials and Methods

Two peptides, p85A (Sequence ID No. 1) and met-p85A (Sequence ID No. 2) were prepared using Fmoc chemistry and a p-hydroxymethylphenoxymethyl polystyrene (HMP) resin having the first amino acid attached. The p85A sequence was chosen from a group of peptides prepared for the production of antisera because it contained no internal methionine residues. The subsequent addition of the methionine linker at the N-terminus provided a convenient chemical cleavage site which would regenerate the p85A sequence upon the removal of the methionine/polymer moiety from met-p85A.

All amino acids (exclusively of the L-stereo configuration) were coupled doubly as the HOBt esters preactivated in the presence of the condensing agent 2 (1H-benzotriazol-1-yl)-1,1,3,3-tetramethyluronium hexafluorophosphate (HBTU). A ten-fold excess of amino acid (1.0 mmol) over resin sites was used. The amino acid is present in slight excess over the HOBt:HBTU to limit the possibility of undesirable side reactions. Each doubly coupled addition was followed by a capping step in which the still unreacted N-termini were irreversibly blocked by reaction with acetic anhydride. Upon completion of the p85A sequence, the resin was divided and one-half was reacted with Fmoc-methionine to produce the met-p85A peptide.

The met-p85A peptide was then PEGylated by reaction of PEG 600. PEG 600 (1.0 mmol) was coupled using the identical reaction used to condense the amino acids, namely as the HOBt ester with HBTU as the condensing agent for 90 minutes at RT. The reaction was judged complete based on a negative quantitative ninhydrin assay [*Anal. Biochem.*, 117:147–157 (1981)]. The p85A control peptide as well as the PEG-met-p85A peptide were released from the resin by chemical cleavage with trifluoroacetic acid (TFA) in the presence of 0.5 mL of 1,2-ethanedithiol and 0.5 mL of thioanisole at room temperature for 200 minutes. The peptides were then precipitated and washed by the addition of cold (4° C.) t-butyl methyl ether. The washed peptide was then dissolved in 20% acetic acid then dried by lyophilization.

The samples were analyzed by reverse-phase high performance liquid chromatography (RP-HPLC) to assess the retention times for the two different forms of the peptide. The control peptide and the PEGylated peptide were dissolved in 20% acetic acid (2.5 mg/ml), and 0.2 mL samples were injected onto a preequilibrated polystyrene-based C4 semi-prep RP-HPLC column (PLRP-S 300 Å, 7.5×50 mm I.D., Polymer Laboratories, Amherst, Mass.). The column was equilibrated in 1% acetonitrile ($CH_3CN$) in deionized-distilled water containing 0.1% TFA at a flow rate of 2.0 mL/min. After maintaining the 1% $CH_3CN$ for three minutes post sample injection, a programmed gradient from 1% $CH_3CN$ to 45% $CH_3CN$ over 30 minutes was then executed. The column was then ramped to 80% $CH_3CN$ followed by a 6-minute hold prior to returning to the initial conditions.

The HPLC fractions were collected and analyzed by matrix assisted laser desorption ionization mass spectrometry (MALDI-MS). RP-HPLC-purified PEGylated peptide and the PEG-crosslinked peptide were isolated in this fashion and taken to dryness by lyophilization. The monosubstituted peptide (10 mg) and the crosslinked peptide (5 mg) were then treated with a 30x excess of cyanogen bromide in 70% formic acid for 15-hour to release the methionine/polymer moiety and regenerate the free peptide. The progress of the reaction was monitored by RP-HPLC and MALDI-MS.

Results

Figure 7:
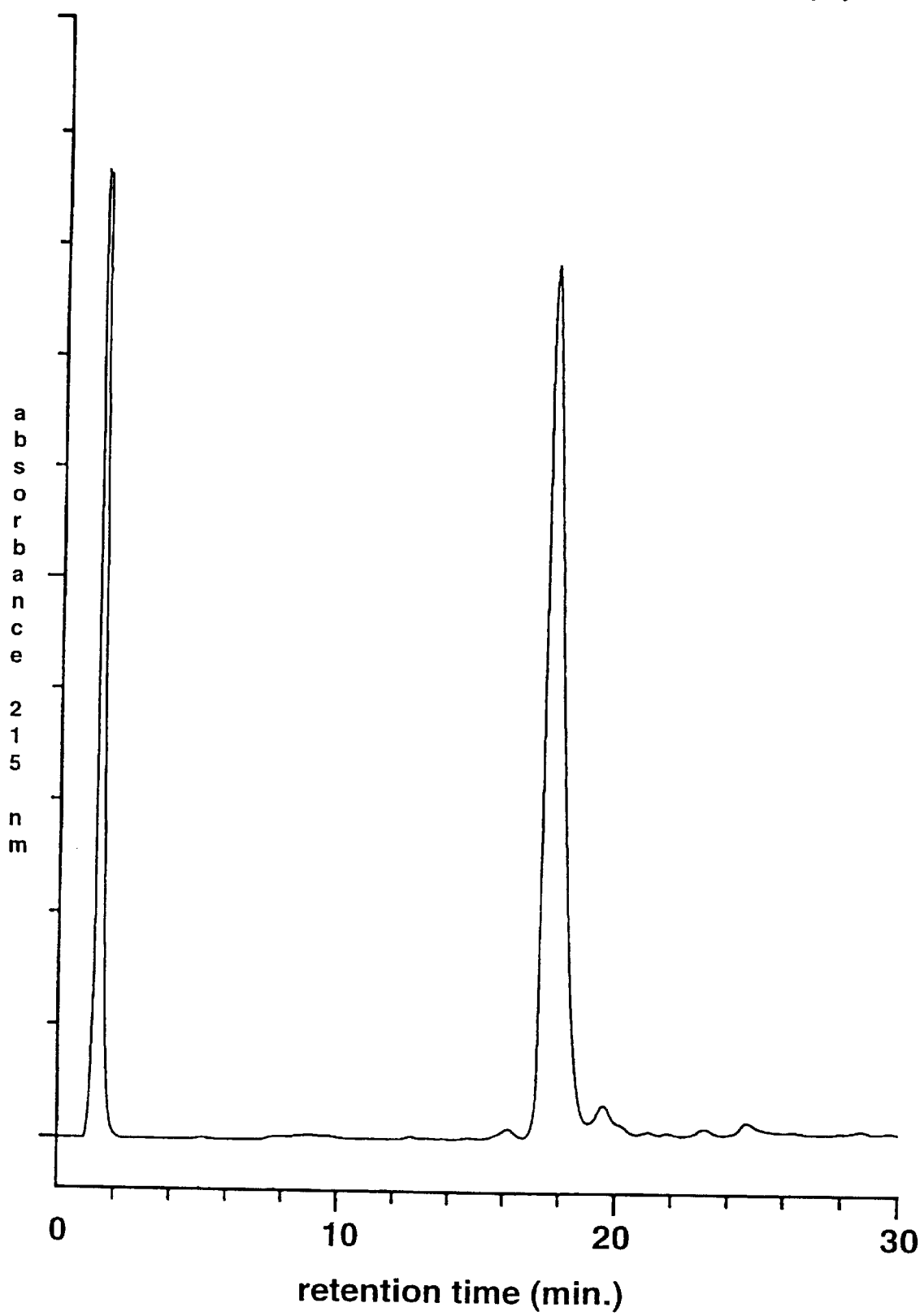
FIG. 7 is a chromatographic profile of untreated peptide p85A.
Figure 8:
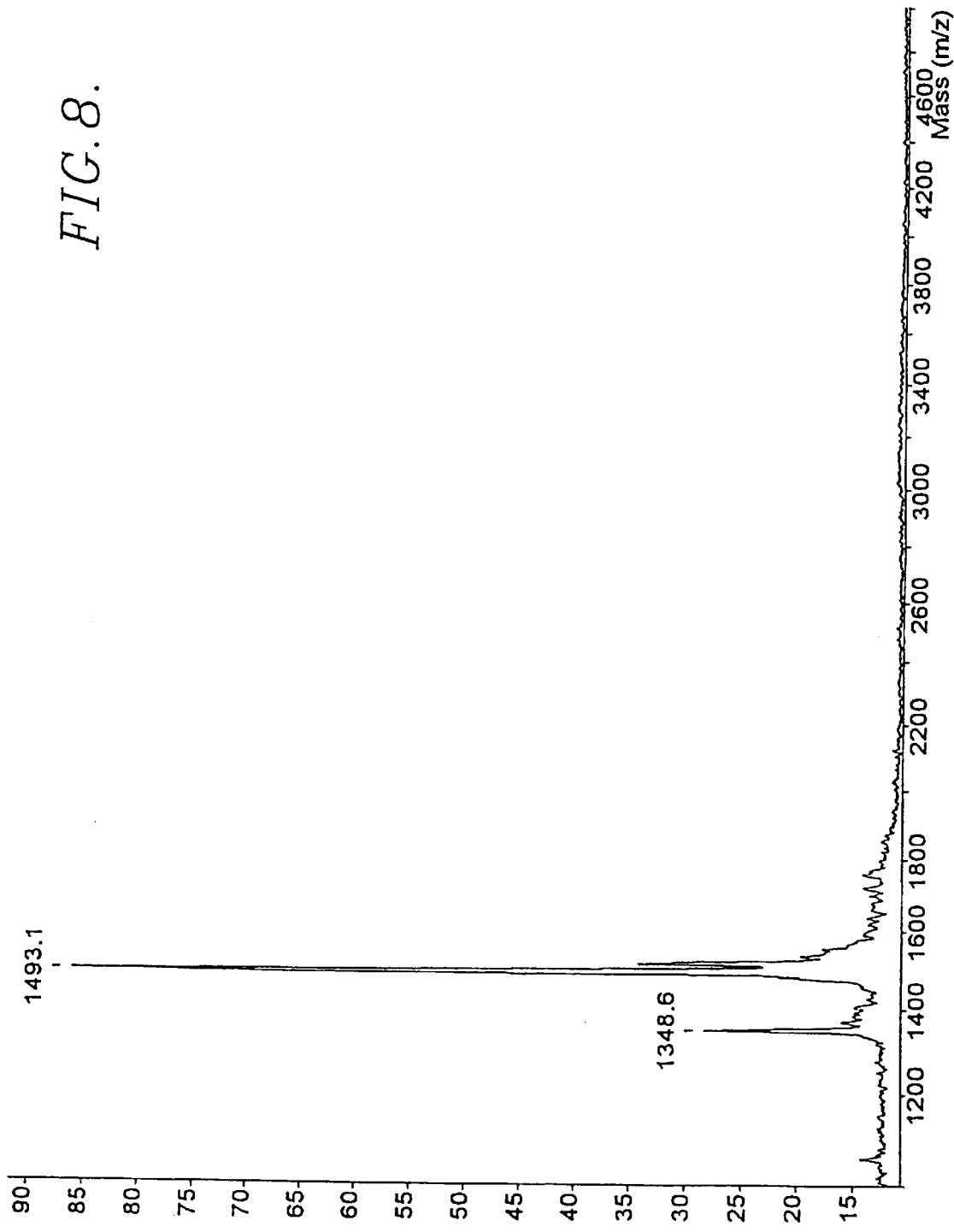
FIG. 8 is a mass spectrum of untreated peptide p85A.
Figure 9:
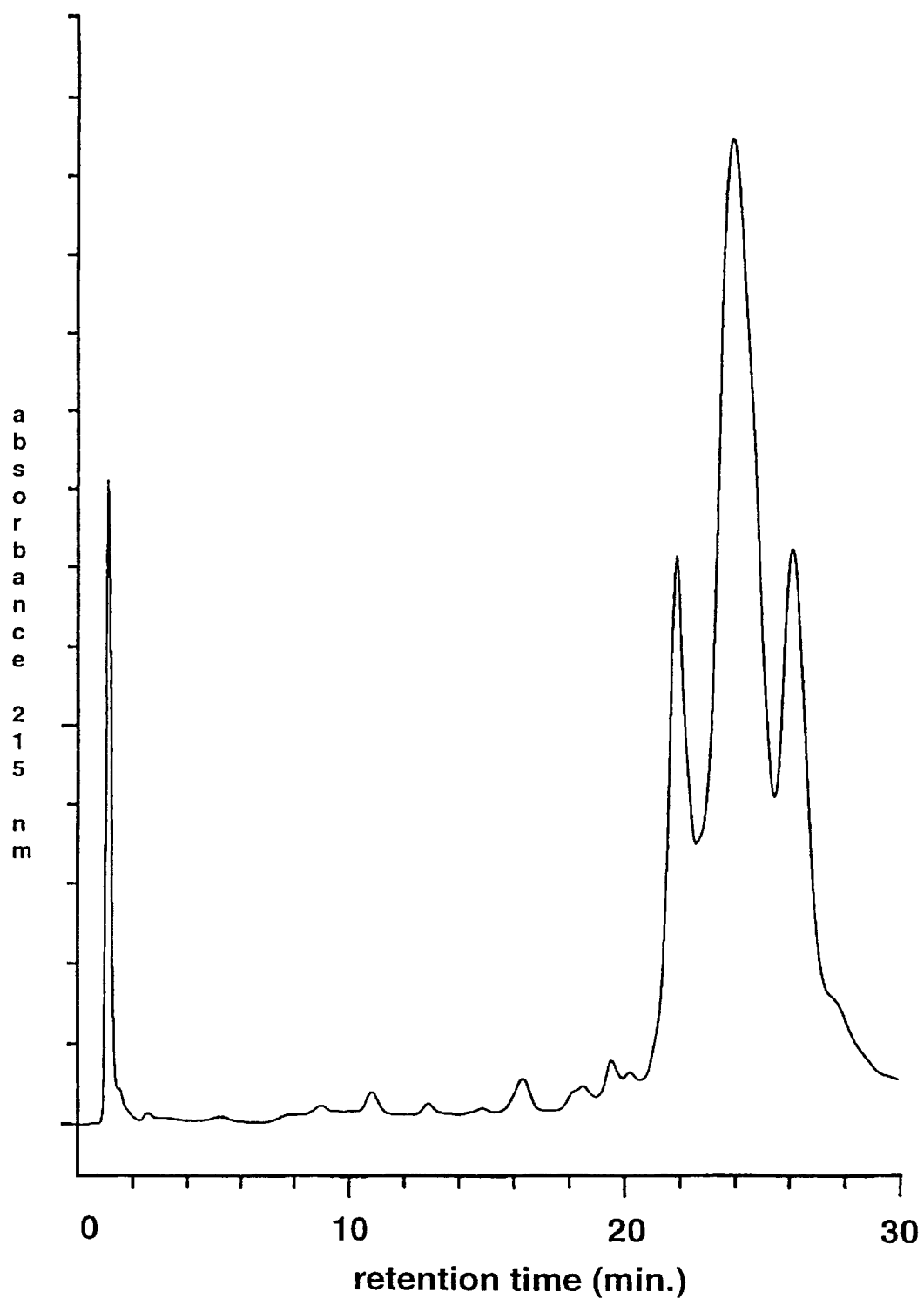
FIG. 9 is a chromatographic profile of reaction products seen after a reaction of peptide met-p85A with Poly(ethylene glycol) bis(carboxymethyl) ether with an average MW ca. 600 (PEG 600) and subsequent cleavage of the peptide from a solid-phase support.
Figure 10:
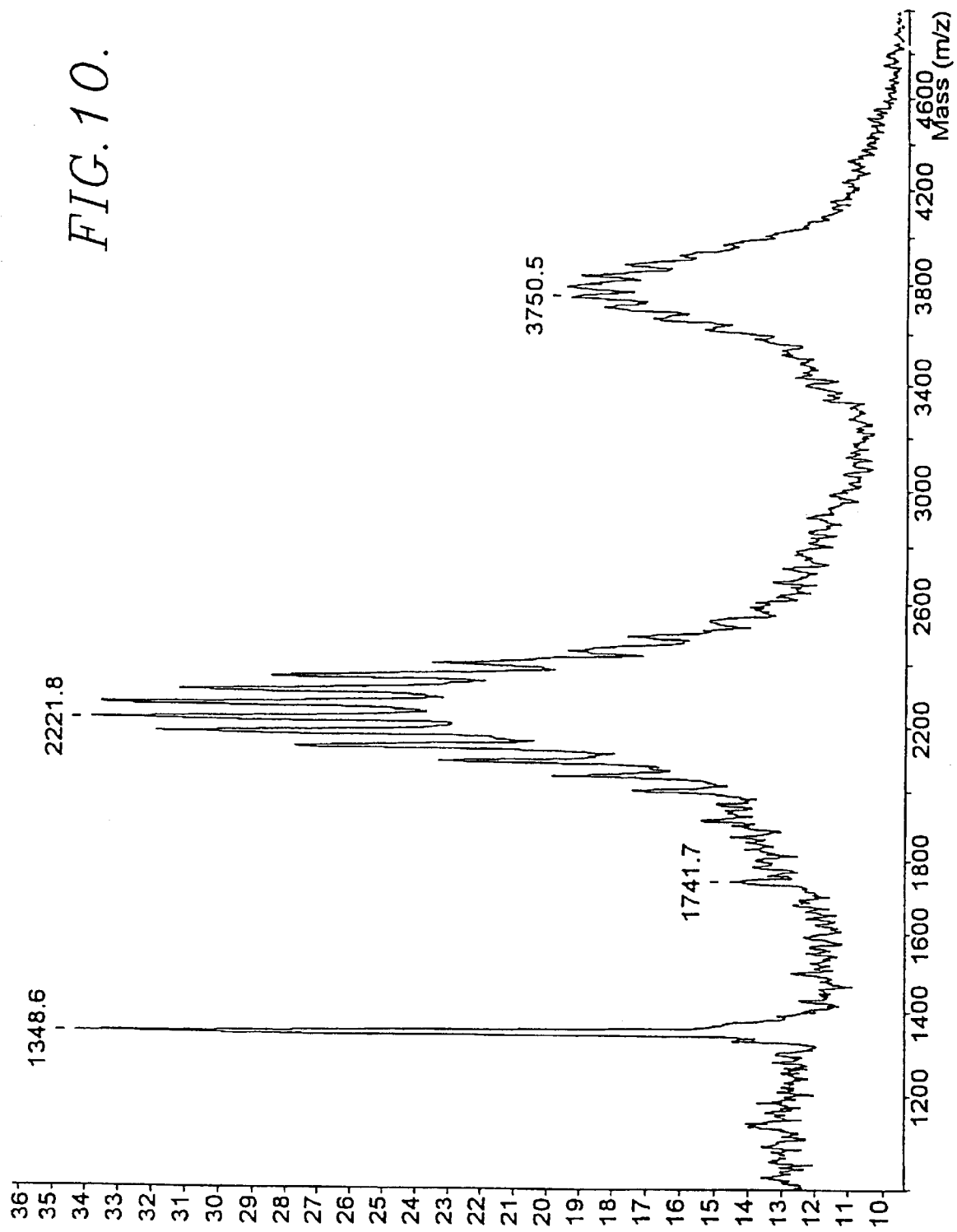
FIG. 10 is a mass spectrum of reaction products seen after a reaction of peptide met-p85A with PEG 600 and subsequent cleavage of the peptide from a solid-phase support.
Figure 11:
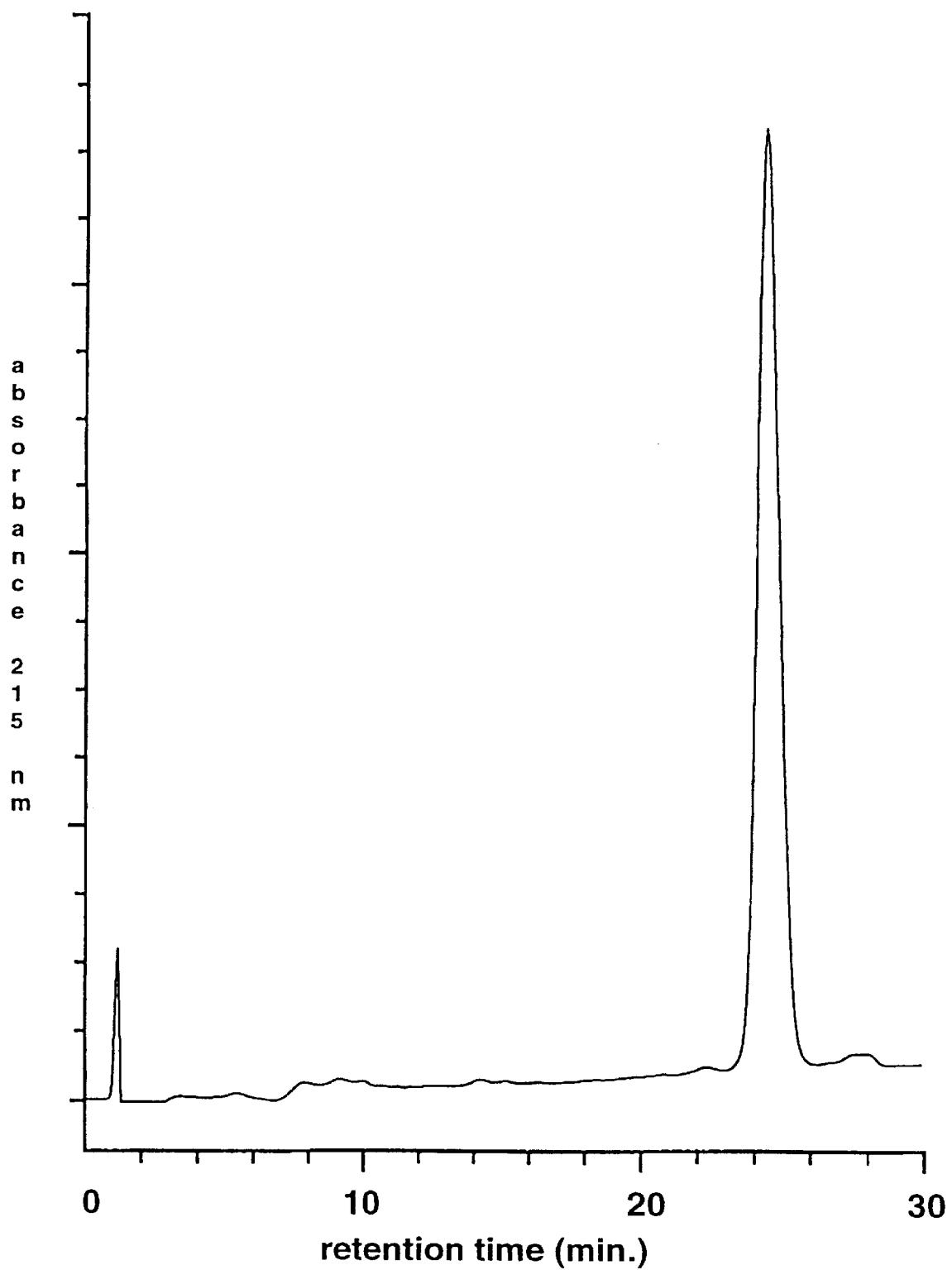
FIG. 11 is a chromatographic profile of a 24-minute fraction of purified monosubstituted PEG-met-p85A.
Figure 12:
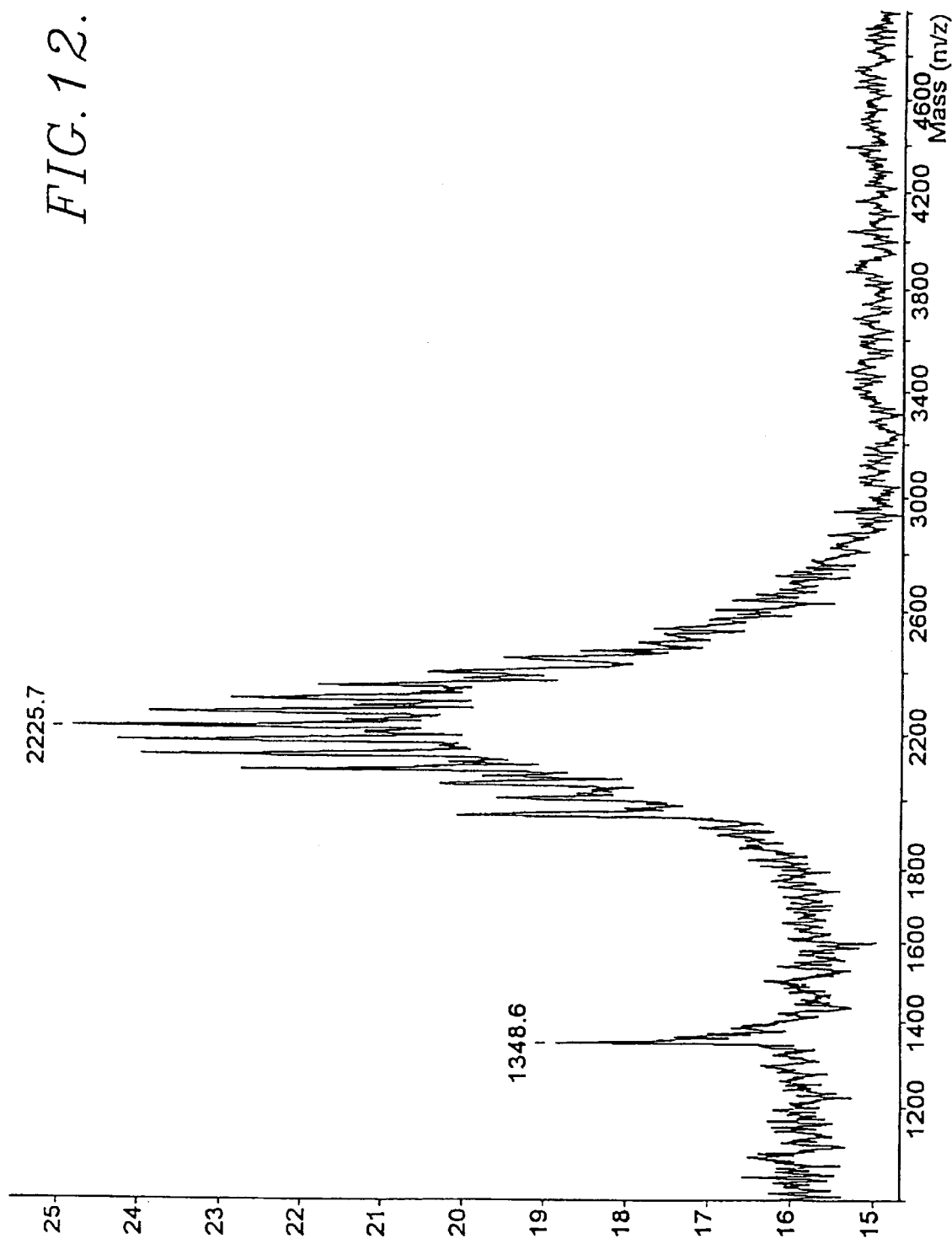
FIG. 12 is a mass spectrum of a 24-minute fraction of purified monosubstituted PEG-met-p85A.

The control peptide, p85A, eluted as a single symmetrical peak with a retention time of 18 minutes (FIG. 7). The principle mass detected for this peptide was 1492.8 (FIG. 8), a value in agreement with the calculated mass of 1492.75. The retention time of PEG 600 overlapped that of the control sequence (data not shown). The PEG-met-p85A reaction mixture showed three peaks eluting later in the gradient. The retention times for the three peaks were 22, 24 and 27 minutes, respectively (FIG. 9). The masses for the peaks contained in the crude pegylated met-p85A sample are shown (FIG. 10). The 22-minute peak gave a single sharp signal at 1741.7 Da. This mass is 118 Da larger than the mass expected for the met-p85A peptide. This peak was not present in the control peptide p85A. Automated Edman degradation indicated that the N-terminus of the peptide is blocked. It is suspected that this alkylation of the peptide may be due to some contaminant in the stock PEG 600 reagent. The 24-minute peak (FIG. 11) which eluted six minutes later in the gradient than either the PEG alone or the free control peptide, gave a broad MS peak with the mass centered about 2250 Da (FIG. 12) and represents the monosubstituted PEG-met-p85A. The peak width reflects the heterogenous nature of the PEG reagent. The 27-minute peak from the RP-HPLC of the PEGylation reaction also gave a broad MS peak, but with the mass centered at 3770. This species represents two met-p85A peptides bridged by one PEG molecule. The length of the PEG 600 relative to the interpeptide spacing on the resin obviously allows for substantial crosslinking of peptides close to one another.

Figure 13:
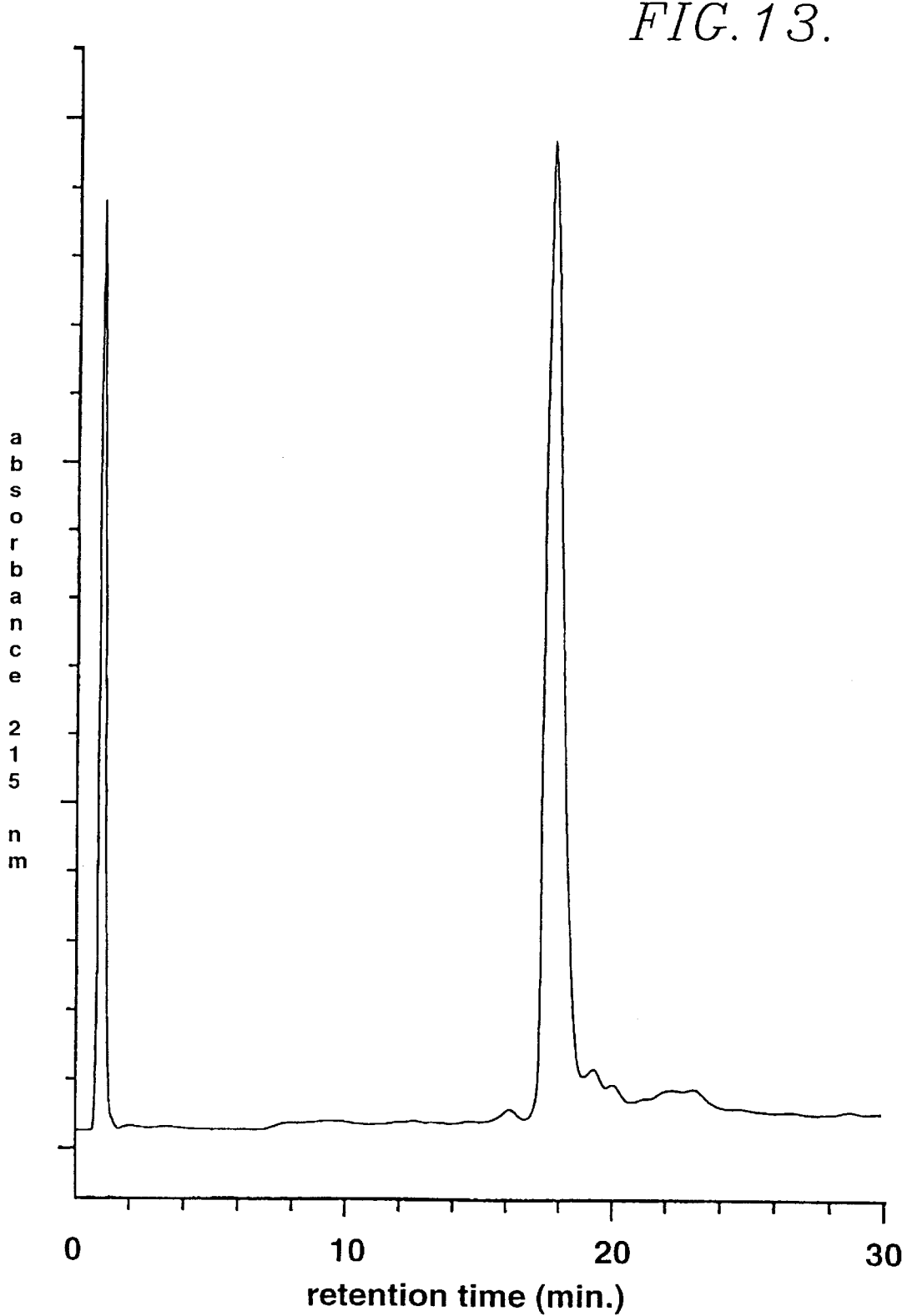
FIG. 13 is a chromatographic profile of a 24-minute fraction of purified monosubstituted PEG-met-p85A after a 4-hour treatment with a 30x excess of cyanogen bromide (CNBr) in 70% formic acid.
Figure 14:
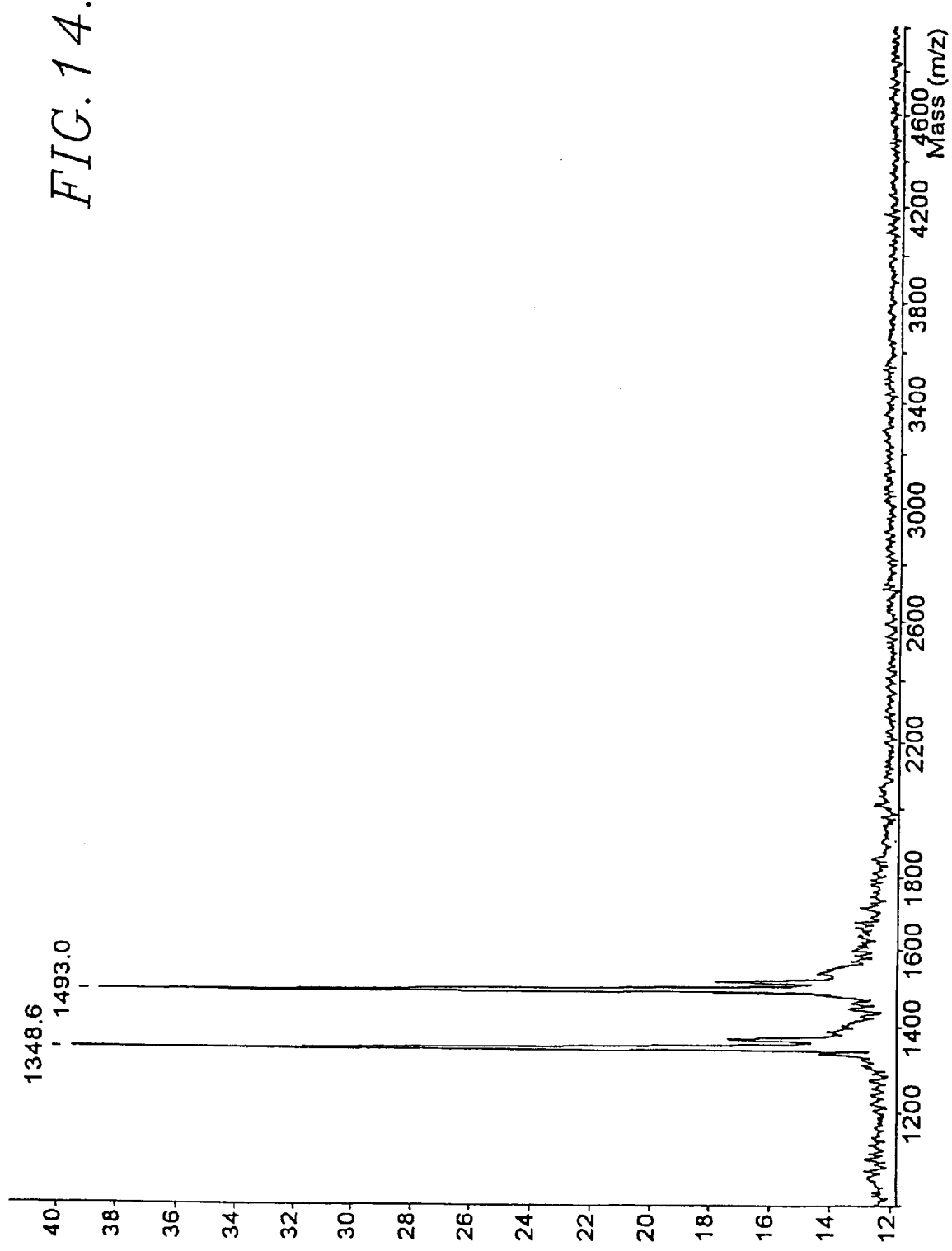
FIG. 14 is a mass spectrum of a 24-minute fraction of purified monosubstituted PEG-met-p85A after a 4-hour treatment with a 30x excess of CNBr in 70% formic acid.

The HPLC chromatogram and the mass of the CNBr-treated monosubstituted PEG-met-p85A peptide is shown in FIGS. 13 and 14, respectively. Release of the PEG-met moiety from the monosubstituted peptide resulted in a peptide that has the identical retention time and mass of the control peptide. None of the released homoserine lactone-PEG was seen in the 18-minute fraction. Release of the met-PEG-met moiety from the PEG-crosslinked peptide by CNBr was also followed. At 4-hour, the HPLC and MS revealed that about one-half of the product was at mass 1492 and the other half had the mass of the monosubstituted peptide. At 15 hours, only the 1492 Da peak was detectable (data not shown). These experiments indicated that the CNBr cleavage reaction is quantitative and that the target sequence can be recovered easily.

We claim:

1. A method for synthesizing a desired peptide comprising the steps of:
   (a) providing a reaction zone including an immobilizing support;
   (b) generating a peptide-bonded chain of multiple amino acid residues with the chain having a C-terminal end bound to the support and presenting a free N-terminal end, by stepwise attachment of amino acid residues until the chain is complete, the chain-generating step comprising the steps of:
      (i) passing a respective amino acid unit including an amino acid residue and a blocking group attached to the amino acid residue through the reaction zone;
      (ii) passing a capping reagent through the reaction zone for capping the previously attached amino acid residue, in the event that the respective amino acid unit fails to attach;
      (iii) detaching the blocking group from the respective amino acid unit; and
      (iv) repeating steps (i), (ii), and (iii) with each of a plurality of amino acid units,
   (c) producing an adduct having increased solubility characteristics over the peptide chain alone including a polymer moiety selected from the group consisting of polyalkylene glycols, polyamides, polystyrenes, polyesters, polyacrylamides, polyalcohols, oligopeptides, oligosaccharides, oligonucleotides, and mixtures thereof attached to the alpha nitrogen atom of the N-terminal amino acid residue of the chain, wherein the polymer moiety has a plurality of repeating chemical groups and is attached directly to the N-terminal amino acid moiety generated in step (b);
   (d) cleaving the adduct from the support; and
   (e) removing the polymer moiety from the adduct to yield a desired peptide.

2. The method of claim 1, wherein the blocking group comprises a 9-fluorenylmethoxycarbonyl group.

3. The method of claim 1, wherein the capping reagent is selected from the group consisting of 4-methoxybenzoic acid or acetic anhydride.

4. The method of claim 1, wherein in step (c), the polymer moiety is formed by attaching a preformed polymer to the N-terminal end of the chain.

5. The method of claim 1, wherein the polymer moiety is a polyalkylene glycol.

6. The method of claim 1, wherein in step (c), the polymer moiety is formed by the in situ polymerization of a monomer at the N-terminal end of the chain.

7. The method of claim 1, comprising the additional step of separating the adduct from undesired peptides after step (d).

8. The method of claim 7, wherein the adduct and the undesired peptides have significantly different solubility characteristics in a selected solvent, and the selected solvent is used in the separating step.

9. The method of claim 1, comprising the additional step of attaching a linker to the free end of the chain prior to step (c), whereby, after step (c), the linker is interposed between the N-terminal end of the chain and the polymer moiety.

10. The method of claim 1, wherein the linker is a methionine residue.

11. The method of claim 1, wherein a polymer is attached to the linker to form a polymer/linker molecule before the linker is attached to the N-terminal end of the chain, whereby step (c) is accomplished by attaching the polymer/linker molecule to the N-terminal end of the chain.

12. The method of claim 11, wherein the polymer/linker molecule is poly-2-amidofluorenyl-9-methoxycarbonyl chloride.

13. The method of claim 1, wherein the desired polymer-peptide adduct includes greater than 30 amino acid residues.

14. The method of claim 1, wherein the desired polymer-peptide adduct includes a helical amphipathic peptide moiety.

15. A method for purifying a desired peptide from undesired peptides comprising the steps of:
   (a) producing an adduct including a polymer moiety attached to the alpha nitrogen atom of the N-terminal amino acid residue of a desired peptide moiety, wherein the polymer moiety is selected from group consisting of polyalkylene glycols, polyamides, polystyrenes, polyesters, polyacrylamides, polyalcohols, oligopeptides, oligosaccharides, oligonucleotides, and mixtures thereof and wherein the polymer moiety has a plurality of repeating chemical groups which give the adduct physicochemical properties different from those of the undesired peptides, said polymer moiety directly attached to the N-terminal amino acid moiety of said desired peptide moiety;
   (b) separating the adduct from the undesired peptides based on said physicochemical differences; and
   (c) removing the polymer moiety from the adduct to yield a desired peptide.

16. The method of claim 15, wherein the desired polymer-peptide adduct and the undesired peptides are attached at their C-terminal ends to an immobilizing support in a reaction vessel.

17. The method of claim 15, wherein in step (a), the polymer moiety is formed by attaching a preformed polymer to the N-terminal end of a desired peptide.

18. The method of claim 17, wherein the polymer moiety is a polyalkylene glycol.

19. The method of claim 15, wherein the polymer moiety is selected from the group consisting of polyalkylene glycols, polyamides, polystyrenes, polyesters, polyacrylamides, polyalcohols, oligopeptides, oligosaccharides, oligonucleotides, and mixtures thereof.

20. The method of claim 15, wherein the adduct and the undesired peptides have significantly different solubility characteristics in a selected solvent, and the selected solvent is used in step (b).

21. The method of claim 15, comprising the additional step of attaching a linker to the N-terminal end of a desired peptide prior to step (a), whereby, after step (a), the linker is interposed between the N-terminal end of the desired peptide moiety and the polymer moiety.

22. The method of claim 21, wherein the linker is a methionine residue.

23. The method of claim 21, wherein a polymer is attached to the linker to form a polymer/linker molecule before the linker is attached to the desired peptide.

24. The method of claim 23, wherein the polymer/linker molecule is poly-2-amidofluorenyl-9-methoxycarbonyl chloride.

25. The method of claim 15, wherein the desired polymer-peptide adduct includes greater than 30 amino acid residues.

26. The method of claim 15, wherein the desired polymer-peptide adduct includes a helical amphipathic peptide moiety.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 12 amino acids
      (B) TYPE: amino acid
      (D) TOPOLOGY: linear (ii) MOLECULE TYPE: peptide (iii) HYPOTHETICAL: NO (xi) SEQUENCE DESCRIPTION: SEQ ID NO:1:

Lys Leu Ala Tyr Pro Val Tyr Ala Gln Gln Arg Arg
   1              5                  10

(2) INFORMATION FOR SEQ ID NO:2:

```
(i) SEQUENCE CHARACTERISTICS:
    (A) LENGTH: 13 amino acids
    (B) TYPE: amino acid
    (D) TOPOLOGY: linear (ii) MOLECULE TYPE: peptide (iii) HYPOTHETICAL: NO (xi) SEQUENCE DESCRIPTION: SEQ ID NO:2:

Met Lys Leu Ala Tyr Pro Val Tyr Ala Gln Gln Arg Arg
 1               5                  10
```